United States Patent [19]

Bofinger et al.

[11] Patent Number: 4,776,973
[45] Date of Patent: Oct. 11, 1988

[54] PYRIMIDINE DERIVATIVES

[75] Inventors: Klaus Bofinger, Mühltal; Michael Römer, Rodgau; Bernhard Scheuble, Alsbach; Georg Weber, Erzhausen, all of Fed. Rep. of Germany

[73] Assignee: Merck Patent Gesellschaft mit Beschrankter Haftung, Darmstadt, Fed. Rep. of Germany

[21] Appl. No.: 832,120

[22] Filed: Feb. 24, 1986

[30] Foreign Application Priority Data

Feb. 23, 1985 [DE] Fed. Rep. of Germany ....... 3506446

[51] Int. Cl.$^4$ .................. C09K 19/34; G02F 1/13; C07D 239/04; 252 299.61; 252 299.5; 252 299.01
[52] U.S. Cl. .................. 252/299.61; 252/299.5; 252/299.01; 350/350 R; 350/350 S; 544/242; 544/298; 544/315; 544/316; 544/318; 544/334; 544/335
[58] Field of Search .......... 350/350 R, 350 S; 544/242, 298, 316, 318, 315, 334, 335; 252/299.61, 299.5, 299.01

[56] References Cited

U.S. PATENT DOCUMENTS

| | | | |
|---|---|---|---|
| 4,311,610 | 1/1982 | Zaschke et al. | 252/299.61 |
| 4,512,636 | 4/1985 | Andrews et al. | 252/299.61 |
| 4,528,114 | 7/1985 | Petrzilka et al. | 252/299.61 |
| 4,564,694 | 1/1986 | Hirai et al. | 252/299.61 |
| 4,621,901 | 11/1986 | Petrzilka et al. | 252/299.61 |
| 4,623,477 | 11/1986 | Ogawa et al. | 252/299.61 |
| 4,630,897 | 12/1986 | Andrews et al. | 252/299.61 |
| 4,632,515 | 12/1986 | Gray et al. | 252/299.61 |
| 4,659,502 | 4/1987 | Fearom et al. | 252/299.61 |
| 4,676,604 | 6/1987 | Petrzilka | 252/299.61 |
| 4,713,197 | 12/1987 | Eibensenike et al. | 252/299.61 |
| 4,723,005 | 2/1988 | Huynh-ba et al. | 252/299.61 |

FOREIGN PATENT DOCUMENTS

| | | | |
|---|---|---|---|
| 56501 | 7/1982 | European Pat. Off. | 252/299.61 |
| 84194 | 7/1983 | European Pat. Off. | 252/299.61 |
| 149238 | 7/1985 | European Pat. Off. | 252/299.61 |
| 3404116 | 8/1985 | Fed. Rep. of Germany | 252/299.61 |
| 3411571 | 10/1985 | Fed. Rep. of Germany | 252/299.61 |
| 3500909 | 7/1986 | Fed. Rep. of Germany | 252/299.61 |
| 8600067 | 6/1985 | PCT Int'l Appl. | 252/299.61 |
| 2092169 | 8/1982 | United Kingdom | 252/299.61 |

Primary Examiner—Teddy S. Gron
Attorney, Agent, or Firm—Millen & White

[57] ABSTRACT

Pyrimidine derivatives of the formula I $$R^1—Pry—A^1—Z^1—A^2-[Z^2—A^3]_m—R^2 \qquad I$$

in which $R^1$ and $R^2$ each are an alkyl group having 1 to 12 C atoms, in which one or two non-adjacent $CH_2$ groups can also be replaced by —O—, —CO—, —O—CO—, —CO—O— or —CH=CH—, and one of the radicals $R^1$ and $R^2$ are H, F, Cl, Br or CN, Pyr is pyrimidine-2,5-diyl, $A^1$ and $A^3$ each are 1,4-cyclohexylene, unsubstituted 1,4-phenylene or 1,4-phenylene which is substituted by one or two F and/or Cl atoms and/or $CH_3$ and /or CN groups, $A^2$ is 1,4-phenylene which is unsubstituted or substituted by one or two F and/or Cl atoms and/or $CH_3$ and/or CN groups, $Z^1$ is —$CH_2CH_2$—, —$CH_2O$—, or —$OCH_2$—

$Z^2$ is —CO—O—, —O—CO—, —$CH_2CH_2$—, —$CH_2O$—, —O—$CH_2$— or a single bond, and m is 0 or 1, are suitable for preparing liquid crystal phases having steep electro-optical characteristic curves.

12 Claims, No Drawings

PYRIMIDINE DERIVATIVES

BACKGROUND OF THE INVENTION

This invention relates to new pyrimidine derivatives. Similar compounds are known for example from German Offenlegungsschrift No. 3,040,632. However, the compounds sepcified there, unlike the present compounds, contain no pyrimidine-2,5-diyl groups.

SUMMARY OF THE INVENTION

It is an object of this invention to provide new stable liquid crystal or mesogenic compounds which are suitable for use as components of liquid crystal phases.

These objects have been achieved by providing new pyrimidine derivatives of the formula I $$R^1\text{—Pyr—}A^1\text{—}Z^1\text{—}A^2\text{—}[Z^2\text{—}A^3]_m\text{—}R^2 \qquad \text{I}$$

in which
$R^1$ and $R^2$ each independently are an alkyl group having 1 to 12 C atoms, in which one or two non-adjacent $CH_2$ groups can also be replaced by —O—, —CO—, —O—CO—, —CO—O— or —CH=CH—, and one of the radicals $R^1$ and $R^2$ can also be H, F, Cl, Br or CN, Pyr is pyrimidine-2,5-diyl, $A^1$ and $A^3$ each independently are 1,4-cyclohexylene, unsubstituted 1,4-phenylene or 1,4-phenylene which is substituted by one or two F and/or Cl atoms and/or $CH_3$ and/or CN groups, $A^2$ is 1,4-phenylene which is unsubstituted or substituted by one or two F and/or Cl atoms and/or $CH_3$ and/or CN groups,
$Z^1$ is —$CH_2CH_2$—, —$CH_2O$—, or —$OCH_2$—
$Z^2$ is —CO—O—, —O—CO—, —$CH_2CH_2$—, —$CH_2O$—, —O—$CH_2$— or a single bond, and
m is 0 or 1.

For simplicity, hereinafter Cy is a 1,4-cyclo-hexylene group and Phe is a 1,4-phenylene group which, if desired, can also be substituted by one or two F and/or Cl atoms and/or $CH_3$ and/or CN groups.

The compounds of the formula I, like similar compounds, can be used as components of liquid crystal phases, in particular for displays which are based on the principle of the twisted cell (TN displays), the guest host effect, the effect of the deformation of aligned phases or the effect of dynamic scattering.

DETAILED DESCRIPTION

It has been found that the compounds of the formula I are highly suitable for use as components of liquid crystal phases. In particular, they can be used to prepare stable liquid crystal phases for TN displays having high multiplex rates.

It was found, surprisingly, that on addition of compounds of the formula I to liquid crystal phases a considerable improvement in the slope of the characteristic curve of the mixture occurred, so that compounds of type I are to be regarded as particularly advantageously suitable substances for preparing liquid crystal mixtures having a steep characteristic curve.

They hence make it possible to develop highly multiplexible mixture with which a twisted cell can be operated in particular in the first Gooch-Tarry transmission minimum. The result is a very small dependence of the contrast on the angle of observation.

The provision of the compounds of the formula I also, very generally, considerably widens the range of liquid crystal compounds which, from various application viewpoints, are suitable for preparing liquid crystal mixtures.

The compounds of the formula I have a wide range of uses. Depending on the choice of substituents, these compounds can be used as base materials of which liquid crystal phases are predominantly composed; but it is also possible to add compounds of the formula I to liquid crystal base materials of other classes of compounds, for example to reduce the dielectric and/or optical anisotropy of such a phase or to improve the elastic properties of such a phase. The compounds of the formula I are also suitable for use as intermediates for preparing other substances which can be used as components of liquid crystal phases.

The compounds of the formula I are colorless in the pure state and form liquid crystal mesophases within a temperature range which is advantageously located for electro-optical use. They are very stable chemically, thermally and to light.

The invention accordingly provides the compounds of the formula I and a process for their preparation, characterised in that a compound which otherwise conforms to the formula I but contains in place of H atoms one or more reducible groups and/or additional C—C bonds is treated with a reducing agent, or, to prepare ethers of the formula I (in which $R^1$ and/or $R^2$ is an alkyl group in which one or two non-adjacent $CH_2$ groups are replaced O atoms and/or Z is a —$OCH_2$— or —$CH_2$—O— group), a corresponding hydroxy compound is etherified.

The invention also provides the use of the compounds of the formula I as components of liquid crystal phases. The invention further provides liquid crystal phases containing at least one compound of the formula I, and liquid crystal display elements, in particular electrooptical display elements, which contain such phases.

Hereinbefore and hereinafter, $R^1$, $R^2$, $A^1$, $A^2$, $A^3$, $Z^1$, $Z^2$ and m have the specified meaning, unless otherwise stated.

The compounds of the formula I correspondingly include compounds of subformulae Ia and Ib (having three rings) and Ic and Id (having four rings):

| | |
|---|---|
| $R^1$—Pyr—Phe—$Z^1$—Phe—$R^2$ | Ia |
| $R^1$—Pyr—Cy—$Z^1$—Phe—$R^2$ | Ib |
| $R^1$—Pyr—Phe—$Z^1$—Phe—$Z^2$—$A^3$—$R^2$ | Ic |
| $R^1$—Pyr—Cy—$Z^1$—Phe—$Z^2$—$A^3$—$R^2$ | Id |

Of these, those of subformulae Ia and Ic are preferred.

The preferred compounds of subformula Ia include those of subformulae Iaa to Iac:

| | |
|---|---|
| $R^1$—Pyr—Phe—$OCH_2$—Phe—$R^2$ | Iaa |
| $R^1$—Pyr—Phe—$CH_2CH_2$—Phe—$R^2$ | Iab |
| $R^1$—Pyr—Phe—$CH_2O$—Phe—$R^2$ | Iac |

Of these, those of subformula Iaa are particularly preferred.

The preferred compounds of subformula Ib include those of subformulae Iba to Ibc:

| | |
|---|---|
| $R^1$—Pyr—Cy—$OCH_2$—Phe—$R^2$ | Iba |

R$^1$—Pyr—Cy—CH$_2$CH$_2$—Phe—R$^2$     Ibb

R$^1$—Pyr—Cy—CH$_2$O—Phe—R$^2$     Ibc

Preferred compounds of subformulae Ic and Id are those of subformulae Ica to Icc:

R$^1$—Pyr—Phe—OCH$_2$—Phe—OCO—Cy—R$^2$     Ica

R$^1$—Pyr—Phe—OCH$_2$—Phe—OCO—Phe—R$^2$     Icb

R$^1$—Pyr—Phe—OCH$_2$—Phe—Cy—R$^2$     Icc

Of these, those of subformula Ica are particularly preferred.

In the compounds of the formulae above and below, R$^1$ and R$^2$ denote preferably alkyl and also alkoxy or oxaalkyl. Preference is also given to compounds of the formula I in which R$^1$ has one of the abovementioned preferred meanings (in particular alkyl) and R$^2$ is CN.

A$^1$ is preferably Phe, particularly preferably 1,4-phenylene.

A$^2$ is preferably unsubstituted 1,4-phenylene and also, if m is 0, preferably 2- or 3-fluoro-1,4-phenylene.

Z$^1$ is preferably —OCH$_2$—.

m is preferably 0.

Z$^2$ is preferably a single bond or —O—CO—, particularly preferably —O—CO—.

A$^3$ is preferably Cy.

The alkyl radicals in the groups R$^1$ and/or R$^2$ can be straight-chain or branched. Preferably they are straight-chain, have 2, 3, 4, 5, 6, 7, 8, 9, 10, 11 or 12 C atoms and accordingly are preferably ethyl, propyl, butyl, pentyl, hexyl, heptyl, octyl, nonyl, decyl, undecyl or dodecyl, and also methyl.

Alkyl radicals R$^1$ and/or R$^2$ in which one ("alkoxy" or "oxaalkyl") or two ("alkoxyalkoxy" or "dioxaalkyl") CH$_2$ groups are replaced by O atoms can be straight-chain or branched. Preferably they are straight-chain, have 2, 3, 4, 5, 6 or 7 C atoms and accordingly are preferably ethoxy, propoxy, butoxy, pentoxy, hexoxy, heptoxy, 2-oxapropyl (=methoxymethyl), 2-, 3- or 4-oxapentyl, 2-, 3-, 4- or 5-oxahexyl, 2-, 3-, 4-, 5- or 6-oxaheptyl, and also methoxy, octoxy, nonoxy, decoxy, 2-, 3-, 4-, 5-, 6-, 7-oxaoctyl, 2-, 3-, 4-, 5-, 6-, 7- or 8-oxanonyl, 2-, 3-, 4-, 5-, 6-, 7-, 8- or 9-oxadecyl, 1,3-dioxabutyl (=methoxymethoxy), 1,3-, 1,4- or 2,4-dioxapentyl, 1,3-, 1,4-, 1,5-, 2,4-, 2,5- or 3,5-dioxahexyl, 1,3-, 1,4-, 1,5-, 1,6-, 2,4-, 2,5-, 2,6-, 3,5-, 3,6- or 4,6-dioxaheptyl.

Compounds of the formula I and of the preceding and following subformulae having branched wing-groups R$^1$ and R$^2$ can occasionally be of importance because of higher solubility in the customary liquid crystal base materials, but in particular for use as chiral dopants when they are optically active. Branched groups of this kind generally contain no more than one chain branching. Preferred branched radicals R$^1$ are isopropyl, 2-butyl (=1-methylpropyl), isobutyl (=2-methylpropyl), 2-methylbutyl, sopentyl (=3-methylbutyl), 2-methylpentyl, 3-methylpentyl, 2-ethylhexyl, 2-propylpentyl, 2-octyl, isopropoxy, 2-methylpropoxy, 2-methylbutoxy, 3-methylbutoxy, 2-methylpentoxy, 3-methylpentoxy, 2-ethylhexoxy, 1-methylhexoxy, 1-methylheptoxy, 2-oxa-3-methylbutyl, 3-oxa-4-methylpentyl, 2-octyloxy.

Of the compounds of the formula I, preference is given to those of the preceding and following subformulae in which at least one of the radicals contained therein has one of the indicated preferred meanings.

Particularly preferred smaller groups of compounds are those of the ormulae I1 to I7:

Alkyl—Pyr—Phe—OCH$_2$—Phe—alkyl     I1

Alkyl—Pyr—Phe—OCH$_2$—Phe—alkoxy     I2

Alkyl—Pyr—Phe—OCH$_2$—Phe—CN     I3

Alkyl—Pyr—Phe—OCH$_2$—Phe—OCO—Cy—alkyl     I4

Alkyl—Pyr—Phe—OCH$_2$—Phe—OCO—Phe—alkyl     I5

Alkyl—Pyr—Phe—OCH$_2$—Phe—OCO—Phe—alkoxy     I6

Alkyl—Pyr—Phe—OCH$_2$—Phe—Cy—alkyl     I7

In the above formulae I1 to I7, alkyl is preferably a straight-chain alkyl group having 2 to 10 C atoms and alkoxy a straight-chain alkoxy group having 2 to 12 C atoms. Preference is also given to compounds of the formulae I1 to I7 in which a 2-oxaalkyl group having 2 to 12 C atoms is present in place of alkoxy.

Of compounds of the formula I, preference is given to those stereoisomers in which the cyclohexane rings are trans-1,4-disubstituted.

The abovementioned formulae include the two possible 2,5-positional isomers with respect to the pyrimidine-2,5-diyl group. Preferably this group is attached to R$^1$ in the 5-position.

Particular preference is given to compounds of the formula I and of the preceding subformulae in which R$^1$ is a straight-chain alkyl group having 1 to 10 C atoms and R$^2$ is a straight-chain alkoxy, oxaalkyl or alkyl group having 2 to 15 C atoms, in particular having 5 to 12 C atoms.

Particular preference is given further to compounds of the formula and of the preceding subformulae in which R$^1$ or R$^2$ is an alkyl, alkoxy or oxaalkyl group having an optically active C atom.

The compounds of the formula I can be prepared by methods known per se, as described in the literature (for example in standard works such as Houben-Weyl, Methoden der Organischen Chemie [Methods of Organic Chemistry], Georg-Thieme-Verlag, Stuttgart) and using reaction conditions which are known and suitable for the reactions mentioned. In these reactions, it is also possible to take advantage of variants known per se which are not specifically mentioned here.

The person skilled in the art can, by using routine methods, find appropriate methods of synthesis in the state of he art (for example German Offenlegungsschriften Nos. 2,344,732, 2,450,088, 2,429,093, 2,502,904, 2,636,684, 2,701,591 and 2,752,957 concerning compounds having 1,4-cyclohexylene and 1,4-phenylene groups and German Offenlegungsschrift No. 3,201,721 concerning compounds having —CH$_2$CH$_2$— bridge members).

The starting materials can, if desired, also be formed in situ by not isolating them from the reaction mixture but immediately reacting them further to form compounds of the formula I.

For instance, the compounds of the formula I can be prepared by reducing a compound which otherwise conforms to the formula I but contains one or more reducible groups and/or C—C bonds in place of H atoms.

Reducible groups are preferably carbonyl groups, in particular keto groups, and also for example free or esterified hydroxyl groups or aromatically bonded halogen atoms. Preferred starting materials for the reduction conform to the formula I but can contain, instead of a cyclohexane ring, a cyclohexene ring or cyclohexanone ring and/or, instead of a —CH₂CH₂— group, a —CH=CH— group and/or, in place of a —CH₂— group, a —CO— group and/or, in place of an H atom, a free or functionally modified (for example in the form of its p-toluenesulphonate) OH group.

The reduction can be effected for example by catalytic hydrogenation at temperatures between 0° and about 200° and pressures between about 1 and 200 bar in an inert solvent, for example an alcohol such as methanol, ethanol or isopropanol, an ether such as tetrahydrofuran (THF) or dioxane, an ester such as ethyl acetate, a carboxylic acid such as acetic acid or a hydrocarbon such as cyclohexane. Suitable catalysts are preferably noble metals such as Pt or Pd, which can be used in the form of oxides (for example PtO₂, PdO), on a support (for example Pd on carbon, calcium carbonate or strontium carbonate) or in finely divided form.

Ketones can also be reduced by the Clemmensen method (using zinc, amalgamated zinc or tin and hydrochloric acid, preferably in aqueous alcoholic solution or in heterogeneous phase with water/toluene at temperatures between about 80° and 120°) or by the Wolff-Kishner method (using hydrazine, preferably in the presence of alkali such as KOH or NaOH in a high-boiling solvent such as diethylene glycol or triethylene glycol at temperatures between about 100° to 200°) to the corresponding compounds of the formula I which contain alkyl groups and/or —CH₂CH₂— bridges.

Ethers of the formula I (in which $R^1$ and/or $R^2$ is an alkyl group in which one or two CH2 groups are replaced by O atoms and/or in which $Z^1$ and/or in which $Z^2$ is a —OCH₂— or a CH₂O— group) are obtainable by etherification of corresponding hydroxy compounds, preferably corresponding phenols, the hydroxy compound preferably being first converted into a corresponding metal derivative, for example by treatment with NaH, NaNH₂, NaOH, KOH, Na₂CO₃ or K₂CO₃ into the corresponding alkali metal alcoholate or alkali metal phenolate. The latter can then be reacted with the corresponding alkyl halide, alkyl sulphonate or dialkyl sulphate, preferably in an inert solvent such as acetone, 1,2-dimethoxyethane, DMF or dimethyl sulphoxide or in an excess of aqueous or aqueous alcoholic NaOH or KOH at temperatures between about 20° and 100°. Compounds of the formula I having an optically active $R^1$ or $R^2$ can be synthesized according to the above described methods by using the respective optically active starting materials.

The liquid crystal phases according to the invention comprise 2 to 25, preferably 3 to 15, components, including at least one compound of the formula I. The other components are preferably selected from the nematic or nematogenic substances, in particular the known substances, of the classes of azoxybenzenes, benzylideneanilines, biphenyls, terphenyls, phenyl or cyclohexyl benzoate, phenyl or cyclohexyl cyclohexane carboxylates, phenylcyclohexanes, cyclohexylbiphenyls, cyclohexylcyclohexanes, cyclohexylnaphthalenes, 1,4-biscyclohexylbenzenes, 4,4'-biscyclohexylbiphenyls, phenylpyrimidines, cyclohexylpyrimidines, phenyldioxanes, cyclohexyldioxanes, phenyl- or cyclohexyl-1,3-dithianes, 1,2-biscyclohexylethanes, 1,2-bisphenylethanes, 1-phenyl-2-cyclohexylethanes, stilbenes which may be halogenated, benzyl phenyl ethers, tolanes and substituted cinnamic acids.

The most important compounds which come into consideration for use as components of such liquid crystal phases can be characterized by the formula II

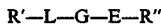

in which L and E are each a carbocyclic or heterocyclic ring system from the group comprising 1,4-disubstituted benzene and cyclohexane rings, 4,4'-disubstituted biphenyl, phenylcyclohexane and cyclohexylcyclohexane systems, 2,5-disubstituted pyrimidine and 1,3-dioxane rings, 2,6-disubstituted naphthalene, dihydronaphthalene, tetrahydronaphthalene, quinazoline and tetrahydroquinazoline

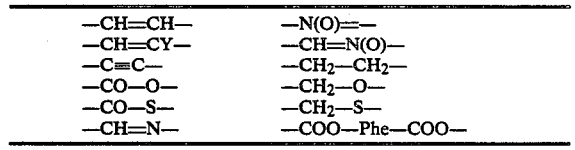

or a C—C single bond, Y is halogen, preferably chlorine, or —CN, and R' and R" are alkyl, alkoxy, alkanoyloxy or alkoxycarbonyloxy having up to 18, preferably up to 8, carbon atoms, or one of these radicals also is CN, NC, NO₂, CF₃, F, Cl or Br.

In most of these compounds, R' and R" are different from each other, one of these radicals usually being an alkyl or an alkoxy group. However, other variants on the proposed substituents are also customary. Many such substances or mixtures thereof are commercially available. All these substances can be prepared by methods described in the literature.

The phases according to the invention contain about 0.1 to 99, preferably 10 to 95, % of one or more compounds of the formula I.

Furthermore, preference is given to dielectrics according to the invention containing 0.1 to 40, preferably 0.5 to 29, % of one or more compounds of the formula I.

The dielectrics according to the invention are prepared in conventional manner. As a rule, the components are dissolved in one another, preferably at elevated temperature.

By means of suitable additives, the liquid crystal dielectrics according to the invention can be modified in such a way that they can be used in all previously disclosed types of liquid crystal display element.

Such additives are known to the person skilled in the art and are extensively described in the literature. It is possible for example to add conductive salts, preferably ethyldimethyldodecylammonium 4-hexyloxybenzoate, tetrabutylammonium tetraphenylboranate or complex salts of crown ethers (cf. for example I. Haller et al., Mol. Cryst. Liq. Cryst. Volume 24, pages 249–258 (1973)) to improve the conductivity, dichroic dyestuffs to prepare colored guest-host systems or substances to modify the dielectric anisotropy, the viscosity and/or the orientation of the nematic phases. Such substances are described for example in German Offenlegungsschriften Nos. 2,209,127, 2,240,864, 2,321,632, 2,338,281, 2,450,088, 2,637,430, 2,853,728 and 2,902,177.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the preceding text and the following examples, all temperatures are set forth uncorrected in degrees Celsius and all parts and percentages are by weight, unless otherwise indicated.

mp=melting point, cp=clear point.

"Conventional working up" means: addition of water, extraction with methylene chloride, separation, drying of the organic phase, evaporation and purification of the product by crystallization and/or chromatography.

EXAMPLE 1

A mixture of 10.2 g of 2-p-hydroxyphenyl-5-n-hexylpyrimidine, 8.6 g of p-n-propylbenzyl bromide, 8.6 g of potassium carbonate and 50 ml of dimethylformamide are heated at 90° for 10 hours. Conventional working up gives 4-(5-n-hexylpyrimidin-2-yl)-phenyl p-n-propylbenzyl ether.

The following are prepared analogously:
4-(5-Hexylpyrimidin-2-yl)-phenyl p-methylbenzyl ether
4-(5-Hexylpyrimidin-2-yl)-phenyl p-ethylbenzyl ether
4-(5-Hexylpyrimidin-2-yl)-phenyl p-butylbenzyl ether
4-(5-Hexylpyrimidin-2-yl)-phenyl p-pentylbenzyl ether mp 72°, cp 104°, S/N 65°, $\Delta\epsilon=+1.0$
4-(5-Hexylpyrimidin-2-yl)-phenyl p-hexylbenzyl ether mp 61°, cp 100.8°, S/N 76°, $\Delta\eta=0.19$
4-(5-Hexylpyrimidin-2-yl)-phenyl p-heptylbenzyl ether
4-(5-Hexylpyrimidin-2-yl)-phenyl p-octylbenzyl ether
4-(5-Hexylpyrimidin-2-yl)-phenyl p-nonylbenzyl ether
4-(5-Hexylpyrimidin-2-yl)-phenyl p-decylbenzyl ether
4-(5-Heptylpyrimidin-2-yl)-phenyl p-methylbenzyl ether
4-(5-Heptylpyrimidin-2-yl)-phenyl p-ethylbenzyl ether
4-(5-Heptylpyrimidin-2-yl)-phenyl p-propylbenzyl ether
4-(5-Heptylpyrimidin-2-yl)-phenyl p-butylbenzyl ether
4-(5-Heptylpyrimidin-2-yl)-phenyl p-pentylbenzyl ether mp 76°, cp 109°, S/N 86°, $\Delta\epsilon=+1.0$
4-(5-Heptylpyrimidin-2-yl)-phenyl p-hexylbenzyl ether mp 48°, cp 107°, S/N 92°, $\Delta\eta=0.19$
4-(5-Heptylpyrimidin-2-yl)-phenyl p-heptylbenzyl ether
4-(5-Heptylpyrimidin-2-yl)-phenyl p-octylbenzyl ether
4-(5-Heptylpyrimidin-2-yl)-phenyl p-nonylbenzyl ether
4-(5-Heptylpyrimidin-2-yl)-phenyl p-decylbenzyl ether
4-(5-Heptylpyrimidin-2-yl)-phenyl p-cyanobenzyl ether
4-(5-Heptylpyrimidin-2-yl)-phenyl p-methoxybenzyl ether
4-(5-Heptylpyrimidin-2-yl)-phenyl p-ethoxybenzyl ether
4-(5-Heptylpyrimidin-2-yl)-phenyl p-butoxybenzyl ether
4-(5-Heptylpyrimidin-2-yl)-phenyl p-hexoxybenzyl ether
4-(5-Heptylpyrimidin-2-yl)-phenyl p-octoxybenzyl ether
4-(5-Octylpyrimidin-2-yl)-phenyl p-methoxybenzyl ether
4-(5-Octylpyrimidin-2-yl)-phenyl p-ethylbenzyl ether
4-(5-Octylpyrimidin-2-yl)-phenyl p-propylbenzyl ether
4-(5-Octylpyrimidin-2-yl)-phenyl p-butylbenzyl ether
4-(5-Octylpyrimidin-2-yl)-phenyl p-pentylbenzyl ether
4-(5-Octylpyrimidin-2-yl)-phenyl p-hexylbenzyl ether
4-(5-Octylpyrimidin-2-yl)-phenyl p-heptylbenzyl ether
4-(5-Octylpyrimidin-2-yl)-phenyl p-octylbenzyl ether
4-(5-Octylpyrimidin-2-yl)-phenyl p-nonylbenzyl ether
4-(5-Octylpyrimidin-2-yl)-phenyl p-decylbenzyl ether
4-(5-Octylpyrimidin-2-yl)-phenyl p-cyanobenzyl ether
4-(5-Octylpyrimidin-2-yl)-phenyl p-methoxybenzyl ether
4-(5-Octylpyrimidin-2-yl)-phenyl p-ethoxybenzyl ether
4-(5-Octylpyrimidin-2-yl)-phenyl p-butoxybenzyl ether
4-(5-Octylpyrimidin-2-yl)-phenyl p-hexoxybenzyl ether
4-(5-Octylpyrimidin-2-yl)-phenyl p-octoxybenzyl ether
4-(5-Nonylpyrimidin-2-yl)-phenyl p-methylbenzyl ether
4-(5-Nonylpyrimidin-2-yl)-phenyl p-ethylbenzyl ether
4-(5-Nonylpyrimidin-2-yl)-phenyl p-propylbenzyl ether
4-(5-Nonylpyrimidin-2-yl)-phenyl p-butylbenzyl ether
4-(5-Nonylpyrimidin-2-yl)-phenyl p-pentylbenzyl ether mp 52°, cp 113°, S/N 107°, $\Delta\epsilon=+0.9$
4-(5-Nonylpyrimidin-2-yl)-phenyl p-hexylbenzyl ether mp 66°, cp 110°, S/N 109°, $\Delta\eta=0.18$
4-(5-Nonylpyrimidin-2-yl)-phenyl p-heptylbenzyl ether, mp 51°, cp 112°
4-(5-Nonylpyrimidin-2-yl)-phenyl p-octylbenzyl ether
4-(5-Nonylpyrimidin-2-yl)-phenyl p-nonylbenzyl ether
4-(5-Nonylpyrimidin-2-yl)-phenyl p-decylbenzyl ether
4-(5-Nonylpyrimidin-2-yl)-phenyl p-cyanobenzyl ether, mp 105°, cp 168°
4-(5-Nonylpyrimidin-2-yl)-phenyl p-methoxybenzyl ether
4-(5-Nonylpyrimidin-2-yl)-phenyl p-ethoxybenzyl ether
4-(5-Nonylpyrimidin-2-yl)-phenyl p-butoxybenzyl ether
4-(5-Nonylpyrimidin-2-yl)-phenyl p-hexoxybenzyl ether
4-(5-Nonylpyrimidin-2-yl)-phenyl p-octoxybenzyl ether
4-(5-Decylpyrimidin-2-yl)-phenyl p-methoxybenzyl ether
4-(5-Decylpyrimidin-2-yl)-phenyl p-ethylbenzyl ether
4-(5-Decylpyrimidin-2-yl)-phenyl p-propylbenzyl ether
4-(5-Decylpyrimidin-2-yl)-phenyl p-butylbenzyl ether
4-(5-Decylpyrimidin-2-yl)-phenyl p-pentylbenzyl ether
4-(5-Decylpyrimidin-2-yl)-phenyl p-hexylbenzyl ether
4-(5-Decylpyrimidin-2-yl)-phenyl p-heptylbenzyl ether
4-(5-Decylpyrimidin-2-yl)-phenyl p-octylbenzyl ether
4-(5-Decylpyrimidin-2-yl)-phenyl p-nonylbenzyl ether
4-(5-Decylpyrimidin-2-yl)-phenyl p-decylbenzyl ether
4-(5-Decylpyrimidin-2-yl)-phenyl p-cyanobenzyl ether
4-(5-Decylpyrimidin-2-yl)-phenyl p-methoxybenzyl ether
4-(5-Decylpyrimidin-2-yl)-phenyl p-ethoxybenzyl ether
4-(5-Decylpyrimidin-2-yl)-phenyl p-butoxybenzyl ether
4-(5-Decylpyrimidin-2-yl)-phenyl p-hexoxybenzyl ether
4-(5-Decylpyrimidin-2-yl)-phenyl p-octoxybenzyl ether
4-(5-Pentylpyrimidin-2-yl)-phenyl p-methylbenzyl ether
4-(5-Pentylpyrimidin-2-yl)-phenyl p-ethylbenzyl ether
4-(5-Pentylpyrimidin-2-yl)-phenyl p-propylbenzyl ether
4-(5-Pentylpyrimidin-2-yl)-phenyl p-butylbenzyl ether
4-(5-Pentylpyrimidin-2-yl)-phenyl p-pentylbenzyl ether
4-(5-Pentylpyrimidin-2-yl)-phenyl p-hexylbenzyl ether
4-(5-Pentylpyrimidin-2-yl)-phenyl p-heptylbenzyl ether
4-(5-Pentylpyrimidin-2-yl)-phenyl p-octylbenzyl ether
4-(5-Pentylpyrimidin-2-yl)-phenyl p-nonylbenzyl ether
4-(5-Pentylpyrimidin-2-yl)-phenyl p-decylbenzyl ether
4-(5-Pentylpyrimidin-2-yl)-phenyl p-cyanobenzyl ether
4-(5-Pentylpyrimidin-2-yl)-phenyl p-methoxybenzyl ether
4-(5-Pentylpyrimidin-2-yl)-phenyl p-ethoxybenzyl ether
4-(5-Pentylpyrimidin-2-yl)-phenyl p-butoxybenzyl ether 4-(5-Pentylpyrimidin-2-yl)-phenyl p-hexoxybenzyl ether
4-(5-Pentylpyrimidin-2-yl)-phenyl p-octoxybenzyl ether
4-(5-Butylpyrimidin-2-yl)-phenyl p-methylbenzyl ether
4-(5-Butylpyrimidin-2-yl)-phenyl p-ethylbenzyl ether
4-(5-Butylpyrimidin-2-yl)-phenyl p-propylbenzyl ether
4-(5-Butylpyrimidin-2-yl)-phenyl p-butylbenzyl ether
4-(5-Butylpyrimidin-2-yl)-phenyl p-pentylbenzyl ether
4-(5-Butylpyrimidin-2-yl)-phenyl p-hexylbenzyl ether
4-(5-Butylpyrimidin-2-yl)-phenyl p-heptylbenzyl ether
4-(5-Butylpyrimidin-2-yl)-phenyl p-octylbenzyl ether
4-(5-Butylpyrimidin-2-yl)-phenyl p-nonylbenzyl ether
4-(5-Butylpyrimidin-2-yl)-phenyl p-decylbenzyl ether
4-(5-Butylpyrimidin-2-yl)-phenyl p-cyanobenzyl ether
4-(5-Butylpyrimidin-2-yl)-phenyl p-methoxybenzyl ether
4-(5-Butylpyrimidin-2-yl)-phenyl p-ethoxybenzyl ether
4-(5-Butylpyrimidin-2-yl)-phenyl p-butoxybenzyl ether
4-(5-Butylpyrimidin-2-yl)-phenyl p-hexoxybenzyl ether
4-(5-Butylpyrimidin-2-yl)-phenyl p-octoxybenzyl ether
4-(5-Propylpyrimidin-2-yl)-phenyl p-methylbenzyl ether
4-(5-Propylpyrimidin-2-yl)-phenyl p-ethylbenzyl ether
4-(5-Propylpyrimidin-2-yl)-phenyl p-propylbenzyl ether
4-(5-Propylpyrimidin-2-yl)-phenyl p-butylbenzyl ether
4-(5-Propylpyrimidin-2-yl)-phenyl p-pentylbenzyl ether
4-(5-Propylpyrimidin-2-yl)-phenyl p-hexylbenzyl ether
4-(5-Propylpyrimidin-2-yl)-phenyl p-heptylbenzyl ether
4-(5-Propylpyrimidin-2-yl)-phenyl p-octylbenzyl ether
4-(5-Propylpyrimidin-2-yl)-phenyl p-nonylbenzyl ether
4-(5-Propylpyrimidin-2-yl)-phenyl p-decylbenzyl ether
4-(5-Propylpyrimidin-2-yl)-phenyl p-cyanobenzyl ether
4-(5-Propylpyrimidin-2-yl)-phenyl p-methoxybenzyl ether
4-(5-Propylpyrimidin-2-yl)-phenyl p-ethoxybenzyl ether
4-(5-Propylpyrimidin-2-yl)-phenyl p-butoxybenzyl ether
4-(5-Propylpyrimidin-2-yl)-phenyl p-hexoxybenzyl ether
4-(5-Propylpyrimidin-2-yl)-phenyl p-octoxybenzyl ether

EXAMPLE 2

To a mixture of 17.8 g of p-n-hexylphenol and 37 g of trans-4-trans-(5-n-hexylpyrimidin-2-yl)-cyclohexylmethanol mesylate [obtainable from the corresponding alcohol which is accessible by reaction of 2-n-hexylpropane-1,3-dialdehyde tetraethyl acetal with trans-4-cyanocyclohexylmethanol or the corresponding amidine by methods described in the literature] in 200 ml of toluene are added 5 g of tetrabutylammonium hydrogen sulphate and 20 ml of 50% NaOH, the mixture is heated with stirring at 70° for three hours and is worked up conventionally, which gives trans-4-(5-n-hexylpyrimidin-2-yl)-cyclohexylmethyl p-n-hexylphenyl ether.

The following are prepared analogously:
trans-4-(5-Hexylpyrimidin-2-yl)-cyclohexylmethyl p-propylphenyl ether
trans-4-(5-Hexylpyrimidin-2-yl)-cyclohexylmethyl p-butylphenyl ether
trans-4-(5-Hexylpyrimidin-2-yl)-cyclohexylmethyl p-pentylphenyl ether
trans-4-(5-Hexylpyrimidin-2-yl)-cyclohexylmethyl p-heptylphenyl ether
trans-4-(5-Hexylpyrimidin-2-yl)-cyclohexylmethyl p-nonylphenyl ether
trans-4-(5-Hexylpyrimidin-2-yl)-cyclohexylmethyl p-decylphenyl ether
trans-4-(5-Pentylpyrimidin-2-yl)-cyclohexylmethyl p-propylphenyl ether
trans-4-(5-Pentylpyrimidin-2-yl)-cyclohexylmethyl p-butylphenyl ether
trans-4-(5-Pentylpyrimidin-2-yl)-cyclohexylmethyl p-pentylphenyl ether
trans-4-(5-Pentylpyrimidin-2-yl)-cyclohexylmethyl p-hexylphenyl ether
trans-4-(5-Pentylpyrimidin-2-yl)-cyclohexylmethyl p-heptylphenyl ether
trans-4-(5-Pentylpyrimidin-2-yl)-cyclohexylmethyl p-octylphenyl ether
trans-4-(5-Pentylpyrimidin-2-yl)-cyclohexylmethyl p-nonylphenyl ether
trans-4-(5-Pentylpyrimidin-2-yl)-cyclohexylmethyl p-decylphenyl ether
trans-4-(5-Pentylpyrimidin-2-yl)-cyclohexylmethyl p-dodecylphenyl ether
trans-4-(5-Pentylpyrimidin-2-yl)-cyclohexylmethyl p-cyanophenyl ether
trans-4-(5-Pentylpyrimidin-2-yl)-cyclohexylmethyl p-cyano-m-fluorophenyl ether
trans-4-(5-Heptylpyrimidin-2-yl)-cyclohexylmethyl p-propylphenyl ether
trans-4-(5-Heptylpyrimidin-2-yl)-cyclohexylmethyl p-butylphenyl ether
trans-4-(5-Heptylpyrimidin-2-yl)-cyclohexylmethyl p-pentylphenyl ether
trans-4-(5-Heptylpyrimidin-2-yl)-cyclohexylmethyl p-hexylphenyl ether
trans-4-(5-Heptylpyrimidin-2-yl)-cyclohexylmethyl p-heptylphenyl ether
trans-4-(5-Heptylyrimidin-2-yl)-cyclohexylmethyl p-octylphenyl ether
trans-4-(5-Heptylpyrimidin-2-yl)-cyclohexylmethyl p-nonylphenyl ether
trans-4-(5-Heptylpyrimidin-2-yl)-cyclohexylmethyl p-decylphenyl ether
trans-4-(5-Heptylpyrimidin-2-yl)-cyclohexylmethyl p-dodecylphenyl ether
trans-4-(5-Heptylpyrimidin-2-yl)-cyclohexylmethyl p-cyanophenyl ether
trans-4-(5-Heptylpyrimidin-2-yl)-cyclohexylmethyl p-cyano-m-fluorophenyl ether
trans-4-(5-Nonylpyrimidin-2-yl)-cyclohexylmethyl p-propylphenyl ether
trans-4-(5-Nonylpyrimidin-2-yl)-cyclohexylmethyl p-butylphenyl ether
trans-4-(5-Nonylpyrimidin-2-yl)-cyclohexylmethyl p-pentylphenyl ether
trans-4-(5-Nonylpyrimidin-2-yl)-cyclohexylmethyl p-hexylphenyl ether
trans-4-(5-Nonylpyrimidin-2-yl)-cyclohexylmethyl p-heptylphenyl ether
trans-4-(5-Nonylpyrimidin-2-yl)-cyclohexylmethyl p-octylphenyl ether
trans-4-(5-Nonylpyrimidin-2-yl)-cyclohexylmethyl p-nonylphenyl ether
trans-4-(5-Nonylpyrimidin-2-yl)-cyclohexylmethyl p-decylphenyl ether
trans-4-(5-Nonylpyrimidin-2-yl)-cyclohexylmethyl p-dodecylphenyl ether
trans-4-(5-Nonylpyrimidin-2-yl)-cyclohexylmethyl p-cyanophenyl ether trans-4-(5-Nonylpyrimidin-2-yl)-cyclohexylmethyl p-cyano-m-fluorophenyl ether
trans-4-(5-Decylpyrimidin-2-yl)-cyclohexylmethyl p-propylphenyl ether
trans-4-(5-Decylpyrimidin-2-yl)-cyclohexylmethyl p-butylphenyl ether
trans-4-(5-Decylpyrimidin-2-yl)-cyclohexylmethyl p-pentylphenyl ether
trans-4-(5-Decylpyrimidin-2-yl)-cyclohexylmethyl p-hexylphenyl ether
trans-4-(5-Decylpyrimidin-2-yl)-cyclohexylmethyl p-heptylphenyl ether
trans-4-(5-Decylpyrimidin-2-yl)-cyclohexylmethyl p-octylphenyl ether
trans-4-(5-Decylpyrimidin-2-yl)-cyclohexylmethyl p-nonylphenyl ether
trans-4-(5-Decylpyrimidin-2-yl)-cyclohexylmethyl p-decylphenyl ether
trans-4-(5-Decylpyrimidin-2-yl)-cyclohexylmethyl p-dodecylphenyl ether
trans-4-(5-Decylpyrimidin-2-yl)-cyclohexylmethyl p-cyanophenyl ether
trans-4-(5-Decylpyrimidin-2-yl)-cyclohexylmethyl p-cyano-m-fluorophenyl ether
trans-4-(5-Dodecylpyrimidin-2-yl)-cyclohexylmethyl p-propylphenyl ether
trans-4-(5-Dodecylpyrimidin-2-yl)-cyclohexylmethyl p-butylphenyl ether
trans-4-(5-Dodecylpyrimidin-2-yl)-cyclohexylmethyl p-pentylphenyl ether
trans-4-(5-Dodecylpyrimidin-2-yl)-cyclohexylmethyl p-hexylphenyl ether
trans-4-(5-Dodecylpyrimidin-2-yl)-cyclohexylmethyl p-heptylphenyl ether
trans-4-(5-Dodecylpyrimidin-2-yl)-cyclohexylmethyl p-octylphenyl ether
trans-4-(5-Dodecylpyrimidin-2-yl)-cyclohexylmethyl p-nonylphenyl ether
trans-4-(5-Dodecylpyrimidin-2-yl)-cyclohexylmethyl p-decylphenyl ether
trans-4-(5-Dodecylpyrimidin-2-yl)-cyclohexylmethyl p-dodecylphenyl ether
trans-4-(5-Dodecylpyrimidin-2-yl)-cyclohexylmethyl p-cyanophenyl ether
trans-4-(5-Dodecylpyrimidin-2-yl)-cyclohexylmethyl p-cyano-m-fluorophenyl ether

EXAMPLE 3

A mixture of 0.04M of p-(5-n-heptalpyrimidin-2-yl)-benzyl bromide [obtainable from the corresponding benzyl alcohol, which is accessible by reaction of 2-n-heptylpropane-1,3-dialdehyde tetraethyl acetal with p-hydroxymethylbenzonitrile or the corresponding amidine by methods described in the literature], 0.04M of 4-cyano-3-fluorophenol, 0.2M of potassium carbonate and 150 ml of 2-butanone is boiled for 48 hours, is cooled down and is worked up in conventional manner. This gives p-(5-n-heptylpyrimidin-2-yl)-benzyl 4-cyano-3-fluorophenyl ether.

The following are prepared analogously:
p-(5-Propylpyrimidin-2-yl)-benzyl 4-cyano-3-fluorophenyl ether
p-(5-Butylpyrimidin-2-yl)-benzyl 4-cyano-3-fluorophenyl ether
p-(5-Pentylpyrimidin-2-yl)-benzyl 4-cyano-3-fluorophenyl ether
p-(5-Hexylpyrimidin-2-yl)-benzyl 4-cyano-3-fluorophenyl ether
p-(5-Octylpyrimidin-2-yl)-benzyl 4-cyano-3-fluorophenyl ether
p-(5-Nonylpyrimidin-2-yl)-benzyl 4-cyano-3-fluorophenyl ether
p-(5-Decylpyrimidin-2-yl)-benzyl 4-cyano-3-fluorophenyl ether
p-(5-Dodecylpyrimidin-2-yl)-benzyl 4-cyano-3-fluorophenyl ether

EXAMPLE 4

According to the example 1 optically active compounds of the formula I are obtained by using the corresponding optically active starting materials.

A mixture of 11.9 g 2-p-hydroxyphenyl-5-n-nonylpyrimidine, 10.2 g p-(2-methylbutoxy)-benzylbromide (obtainable from 4-hydroxybenzaldehyde and 2-methylbutylmesylate in the presence of potassium carbonate in dimethylformamide, subsequently reduction of the benzaldehyde to the corresponding benzyl-alcohol and conversion with $PBr_3$ to the corresponding benzylbromide), 8.6 g of potassium carbonate and 50 ml of dimethylformamide are heated at 90° for 10 hours. Conventional working up gives 4-(5-n-nonylpyrimidin-2-yl)-phenyl-[p-(2-methylbutoxy)benzylether], S-Ch 103°, Ch-I 105°.

The following are prepared analogously:
4-(5-n-Hexylpyrimidin-2-yl)-phenyl-[p-(2-methylbutoxy)benzyl ether]
4-(5-n-Heptylpyrimidin-2-yl)-phenyl-[p-(2-methylbutoxy)benzyl ether]
4-(5-n-Octylpyrimidin-2-yl)-phenyl-[p-(2-methylbutoxy)benzyl ether]
4-(5-n-Decylpyrimidin-2-yl)-phenyl-[p-(2-methylbutoxy)benzyl ether]
4-(5-n-Pentylpyrimidin-2-yl)-phenyl-[p-(2-methylbutoxy)benzyl ether]
4-(5-n-Butylpyrimidin-2-yl)-phenyl-[p-(2-methylbutoxy)benzyl ether]
4-(5-n-Propylpyrimidin-2-yl)-phenyl-[p-(2-methylbutoxy)benzyl ether]

EXAMPLE 5

According to the example 4 4-(5-n-nonylpyrimidin-2-yl)phenyl-[p-(2-methylbutoxycarbonyl)benzyl ether] is prepared from 2-p-hydroxyphenyl-5-n-nonylpyrimidine and p-bromomethyl(2-methylbutyl)benzoate (obtainable from p-bromomethylbenzoic acid and 2-methyl-1-butanol by esterification), mp 29°. The following are prepared analogously:
4-(5-Hexylpyrimidin-2-yl)-phenyl-[p-(2-methylbutoxycarbonyl)benzylether]
4-(5-Heptylpyrimidin-2-yl)-phenyl-[p-(2-methylbutoxycarbonyl)benzylether]
4-(5-Octylpyrimidin-2-yl)-phenyl-[p-(2-methylbutoxycarbonyl)benzylether]
4-(5-Decylpyrimidin-2-yl)-phenyl-[p-(2-methylbutoxycarbonyl)benzylether]
4-(5-Pentylpyrimidin-2-yl)-phenyl-[p-(2-methylbutoxycarbonyl)benzylether]
4-(5-Butylpyrimidin-2-yl)-phenyl-[p-(2-methylbutoxycarbonyl)benzylether]
4-(5-Propylpyrimidin-2-yl)-phenyl-[p-(2-methylbutoxycarbonyl)benzylether]

The following examples concern liquid crystal phases according to the invention:

EXAMPLE A

A liquid crystal phase consisting of

5% of 2-p-cyanophenyl-5-ethyl-1,3-dioxane,
8% of 2-p-cyanophenyl-5-propyl-1,3-dioxane,
8% of 2-p-cyanophenyl-5-butyl-1,3-dioxane,
5% of 2-p-cyanophenyl-5-pentyl-1,3-dioxane,
5% of 4-(5-hexylpyrimidin-2-yl)-phenyl p-pentylbenzyl ether,
12% of 4-(5-hexylpyrimidin-2-yl)-phenyl p-hexylbenzyl ether,
11% of 4-(5-heptylpyrimidin-2-yl)-phenyl p-pentylbenzyl ether,
5% of 4,4'-bis-(trans-4-pentylcyclohexyl)-biphenyl,
11% of trans-1-p-methoxyphenyl-4-propylcyclohexane,
5% of 2-p-methoxyphenyl-5-hexylpyrimidine,
5% of 2-p-pentyloxyphenyl-5-hexylpyrimidine,
5% of 2-p-heptyloxyphenyl-5-hexylpyrimidine,
5% of 2-p-methoxyphenyl-5-heptylpyrimidine,
5% of 2-p-heptyloxyphenyl-5-heptylpyrimidine and
5% of 2-p-nonyloxyphenyl-5-heptylpyrimidine has a melting point of $-10°$ and a clear point of 56°.

EXAMPLE B

A liquid crystal phase consisting of
5% of 2-p-cyanophenyl-5-ethyl-1,3-dioxane,
7% of 2-p-cyanophenyl-5-propyl-1,3-dioxane,
8% of 2-p-cyanophenyl-5-butyl-1,3-dioxane,
7% of 2-p-cyanophenyl-5-pentyl-1,3-dioxane,
5% of 4-(5-hexylpyrimidin-2-yl)-phenyl p-pentylbenzyl ether,
10% of 4-(5-heptylpyrimidin-2-yl)-phenol p-pentylbenzyl ether,
8% of 4-(5-heptylpyrimidin-2-yl)-phenyl p-hexylbenzyl ether,
5% of 4-(trans-4-pentylcyclohexyl)-4'-(trans-4-propylcyclohexyl)-2-fluorobiphenyl,
5% of 4,4'-bis-(trans-4-pentylcyclohexyl)-2-fluorobiphenyl,
10% of trans-1-p-methoxyphenyl-4-propylcyclohexane,
5% of 2-p-methoxyphenyl-5-hexylpyrimidine,
5% of 2-p-pentyloxyphenyl-5-hexylpyrimidine,
5% of 2-p-heptyloxyphenyl-5-hexylpyrimidine,
5% of 2-p-methoxyphenyl-5-heptylpyrimidine,
5% of 2-p-heptyloxyphenyl-5-heptylpyrimidine and
5% of 2-p-nonyloxyphenyl-5-heptylpyrimidine
has a melting point of $-14°$, a clear point of 65° and a relatively high optical anisotropy.

EXAMPLE C

A liquid crystal phase consisting of
8% of 4-butyl-4'-cyanobiphenyl,
11% of 4-pentyl-4'-cyanobiphenyl,
8% of 4-hexyl-4'-cyanobiphenyl,
5% of 4-(5-hexylpyrimidin-2-yl)-phenyl p-pentylbenzyl ether,
10% of 4-(5-heptylpyrimidin-2-yl)-phenyl p-pentylbenzyl ether,
8% of 4-(5-heptylpyrimidin-2-yl)-phenyl p-hexylbenzyl ether,
5% of 4-(trans-4-pentylcyclohexyl)-4'-(trans-4-propylcyclohexyl)-2-fluorobiphenyl,
5% of 4,4'-bis-(trans-4-pentylcyclohexyl)-2-fluorobiphenyl,
10% of trans-1-p-methoxyphenyl-4-propylcyclohexane,
5% of 2-p-methoxyphenyl-5-hexylpyrimidine,
5% of 2-p-pentyloxyphenyl-5-hexylpyrimidine,
5% of 2-p-heptyloxyphenyl-5-hexylpyrimidine,
5% of 2-p-methoxyphenyl-5-heptylpyrimidine,
5% of 2-p-heptyloxyphenyl-5-heptylpyrimidine and
5% of 2-p-nonyloxyphenyl-5-heptylpyrimidine
has a melting point of $-13°$, a clear point of 63° and a relatively high optical anistropy.

EXAMPLE D

A liquid crystal phase consisting of
5% of 2-p-cyanophenyl-5-pentylpyrimidine,
10% of 2-p-cyanophenyl-5-heptylpyrimidine,
6% of 2-p-cyanophenyl-5-(p-butylphenyl)-pyrimidine,
6% of 4-(5-hexylpyrimidin-2-yl)-phenyl p-pentylbenzyl ether,
13% of 4-(5-heptylpyrimidin-2-yl)-phenyl p-pentylbenzyl ether,
10% of 4-(5-heptylpyrimidin-2-yl)-phenyl p-hexylbenzyl ether,
5% of 4-(trans-4-pentylcyclohexyl)-4'-(trans-4-propylcyclohexyl)-2-fluorobiphenyl,
5% of 4,4'-bis-(trans-4-pentylcyclohexyl)-2-fluorobiphenyl,
10% of trans-1-p-methoxyphenyl-4-propylcyclohexane,
5% of 2-p-methoxyphenyl-5-hexylpyrimidine,
5% of 2-p-pentyloxyphenyl-5-hexylpyrimidine,
5% of 2-p-heptyloxyphenyl-5-hexylpyrimidine,
5% of 2-p-methoxyphenyl-5-heptylpyrimidine,
5% of 2-p-heptyloxyphenyl-5-heptylpyrimidine and
5% of 2-p-nonyloxyphenyl-5-heptylpyrimidine
has a melting point of $-5°$, a clear point of 85°, a relatively high optical anisotropy and a particularly low threshold voltage.

EXAMPLE E

A liquid crystal phase is prepared from
17% of p-trans-4-propylcyclohexylbenzonitrile,
23% of p-trans-4-pentylcyclohexylbenzonitrile,
16% of trans-1-p-ethoxyphenyl-4-propylcyclohexane,
14% of trans-1-p-butoxyphenyl-4-propylcyclohexane,
10% of 4-(trans-4-pentylcyclohexyl)-4'-(trans-4-propylcyclohexyl)-biphenyl,
10% of 2-(4-ethoxyphenyl)-5-(trans-4-propylcyclohexyl)pyrimidine and
10% of 4-(5-heptylpyrimidin-2-yl)-phenyl p-hexylbenzyl ether.

EXAMPLE F

A liquid crystal phase is prepared from
21% of p-trans-4-ethylcyclohexylbenzonitrile,
22% of p-trans-4-butylcyclohexylbenzonitrile,
14% of 4-ethyl-4'-cyanobiphenyl,
18% of 4-butyl-4'-cyanobiphenyl,
10% of p-pentylphenyl 2-(trans-4-propylcyclohexyl)-pyrimidine-5-carboxylate,
10% of 4-(5-hexylpyrimidin-2-yl)-phenyl p-pentylbenzyl ether and
5% of 4-(5-heptylpyrimidin-2-yl)-phenyl p-hexylbenzyl ether.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention do adapt it to various usages and conditions.

What is claimed is:
1. A pyrimidine compound of the formula

wherein
each of $R^1$ and $R^2$ independently is alkyl of 1 to 12C atoms, or alkyl of 1–12C atoms in which one or two non-adjacent $CH_2$ groups are replaced by —O—, —CO—, —O—CO— or —CO—O— and one of $R^1$ and $R^2$ can also be H, F, Cl or Br, Pyr is pyrimidine-2,5-diyl, $A^1$ is 1,4-cyclohexylene (Cy) or 1,4-phenylene (Phe), $A^2$ is 1,4-phenylene, and $Z^1$ is —$CH_2CH_2$—, —$CH_2O$— or —$OCH_2$—.

2. A compound of claim 1 of the formula
$R^1$—Pyr—Phe—$OCH_2$—Phe—$R^2$,
$R^1$—Pyr—Phe—$CH_2CH_2$—Phe—$R^2$, or
$R^1$—Pyr—Phe—$CH_2O$—Phe—$R^2$.

3. A compound of claim 1 of the formula
$R^1$—Pyr—Cy—$OCH_2$—Phe—$R^2$,
$R^1$—Pyr—Cy—$CH_2CH_2$—Phe—$R^2$, or
$R^1$—Pyr—Cy—$CH_2O$—Phe—$R^2$.

4. A compound of claim 1 wherein $R^1$ and $R^2$ are alkyl, alkoxy or oxaalkyl.

5. A compound of claim 1 wherein $Z^1$ is —$CH_2$—$CH_2$—.

6. A compound of claim 4 wherein $Z^1$ is —$CH_2$—O— or —O—$CH_2$—.

7. A compound of claim 1 wherein $Z^1$ is —$OCH_2$—.

8. A compound of claim 1 of the formula
Alkyl—Pyr—Phe—$OCH_2$—Phe—alkyl or
Alkyl—Pyr—Phe—$OCH_2$—Phe—alkoxy.

9. A compound of claim 4 wherein $R^1$ or $R^2$ has an optically active C-atom.

10. In a liquid crystal phase comprising at least two liquid crystal components, the improvement wherein at least one component is a compound of claim 1.

11. In a liquid crystal display element, comprising a liquid crystal phase, the improvement wherein the phase is of claim 10.

12. In an electro-optical display element comprising a liquid crystalline dielectric, the improvement wherein the dielectric is a phase of claim 10.

* * * * *